(12) United States Patent
Lin et al.

(10) Patent No.: US 11,879,888 B2
(45) Date of Patent: Jan. 23, 2024

(54) GLYCOSURIA MEASUREMENT DEVICE

(71) Applicant: Taiwan RedEye Biomedical Inc., Hsinchu (TW)

(72) Inventors: Tsung-Jui Lin, Hsinchu (TW); Yu-Hsun Chen, Hsinchu (TW); Shuo-Ting Yan, Hsinchu (TW)

(73) Assignee: TAIWAN REDEYE BIOMEDICAL INC., Hsinchu (TW)

( * ) Notice: Subject to any disclaimer, the term of this patent is extended or adjusted under 35 U.S.C. 154(b) by 280 days.

(21) Appl. No.: 17/566,474

(22) Filed: Dec. 30, 2021

(65) Prior Publication Data

US 2023/0213498 A1 Jul. 6, 2023

(51) Int. Cl.
| | |
|---|---|
| *G01N 33/493* | (2006.01) |
| *G02B 5/04* | (2006.01) |
| *G01N 21/31* | (2006.01) |
| *A61B 5/145* | (2006.01) |
| *A61B 5/1455* | (2006.01) |

(52) U.S. Cl.
CPC ......... *G01N 33/493* (2013.01); *A61B 5/1455* (2013.01); *A61B 5/14507* (2013.01); *A61B 5/14532* (2013.01); *G01N 21/31* (2013.01); *G02B 5/04* (2013.01); *G01N 2201/0634* (2013.01)

(58) Field of Classification Search
CPC ...... G01N 33/493; G01N 21/31; G01N 21/41; G01N 21/59; G01N 2201/0634; A61B 5/14507; A61B 5/14532; A61B 5/1455; A61B 5/0075; G02B 5/04

See application file for complete search history.

(56) References Cited

U.S. PATENT DOCUMENTS

| | | | |
|---|---|---|---|
| 9,500,584 B2 | 11/2016 | Neijzen et al. | |
| 10,209,195 B2 | 2/2019 | Jian | |
| 2004/0201835 A1 | 10/2004 | Coates et al. | |
| 2016/0084759 A1 | 3/2016 | Hall et al. | |
| 2016/0299058 A1* | 10/2016 | Li | G01N 21/21 |
| 2017/0138851 A1* | 5/2017 | Ashrafi | G01N 33/487 |

(Continued)

FOREIGN PATENT DOCUMENTS

TW 201506379 A 2/2015

*Primary Examiner* — Tarifur R Chowdhury
*Assistant Examiner* — Carlos Perez-Guzman
(74) *Attorney, Agent, or Firm* — RABIN & BERDO, P.C.

(57) ABSTRACT

The invention discloses a glycosuria measurement device, comprising a prism body and a housing. The prism body comprises a first accommodating space, a junction surface, a first light penetrating surface, a second light penetrating surface, a third light penetrating surface and a light-emitting surface. The first accommodating space accommodates urine. The junction surface is formed at a bottom surface of the first accommodating space. The first light penetrating surface is formed at the first lateral surface of the first accommodating space. The second light penetrating surface is formed at the second lateral surface of the first accommodating space. The third light penetrating surface is disposed opposite to the junction surface. The light-emitting surface is disposed opposite to the junction surface. The housing comprises a second accommodating space, a first light-emitting port and a second light-emitting port. The second accommodating space accommodates the prism body.

10 Claims, 13 Drawing Sheets

(56) References Cited

U.S. PATENT DOCUMENTS

2017/0176255 A1* 6/2017 Nciri ................. G01J 3/0224
2020/0348225 A1* 11/2020 Coates ................ G01J 3/457
2023/0064160 A1* 3/2023 Lin .................... G01N 21/05

* cited by examiner

GLYCOSURIA MEASUREMENT DEVICE

BACKGROUND OF THE INVENTION

1. Field of the Invention

The disclosure relates to a measurement device, and more particularly, a glycosuria measurement device.

2. Description of the Related Art

A high value of glycosuria represents that a volume of glomerulus and glucose passing through blood are so great that a renal tubule cannot absorb the total volume. Therefore, the volume of glomerulus and glucose exhausted by urine is called glycosuria. Generally speaking, when blood glucose exceeds 180 mg/dL, urine will contain glucose. If a result of glycosuria testing is positive, a subject may have risks of diabetes, pancreatitis, liver disease, thyroid disease, and so on.

The high value of glycosuria is normally judged as the factor of high blood glucose. Since the current testing for blood glucose is done by drawing blood, which is intrusive, the subject will have psychological burden, reducing the willingness to get tested. Accordingly, as the subject delays the testing for blood glucose, the high value of blood glucose is detected much later, leading to the aforementioned diseases.

Moreover, the main testing for glycosuria comprises the enzymatic method, wherein a test strip of glucose oxidase method is widely used. Although the cost of test strip is cheap, the testing of the test strip takes 30 to 60 seconds for the subject. Therefore, the testing is not real-time. In addition, the color judgement of the test strip by human eyes is not accurate and the efficiency is lower. Simultaneously, the test strip cannot be conserved for a long time and is prone to deterioration because of air and moisture. Accordingly, the efficacy of the test strip for glycosuria cannot maintain steady.

Since diabetes is a serious problem among the general public, how to provide a non-invasive detective device to detect glycosuria to solve the problems mentioned above is an urgent subject to tackle.

SUMMARY OF THE INVENTION

To overcome aforementioned problems, the invention discloses a glycosuria measurement device, comprising a prism body and a housing. The prism body comprises a first accommodating space, a junction surface, a first light penetrating surface, a second light penetrating surface, a third light penetrating surface, a light-emitting surface, and a light-incident surface. The first accommodating space accommodates urine. The junction surface is formed on a bottom surface of the first accommodating space. The first light penetrating surface is formed on a first lateral surface of the first accommodating space. The second light penetrating surface is formed on a second lateral surface of the first accommodating space opposite to the first light penetrating surface. The third light penetrating surface is disposed opposite to the junction surface. The light-emitting surface is disposed opposite to the junction surface. The light-incident surface is disposed adjacent to the junction surface. The housing comprises a second accommodating space, a first light-emitting port, and a second light-emitting port. The second accommodating space accommodates the prism body. The first light-emitting port has a first diameter and is disposed opposite to the light-emitting surface of the prism body. The second light-emitting port has a second diameter and is disposed opposite to the first light-emitting port. The first diameter is less than or equal to the second diameter. When a first incident beam is emitted through the light-incident surface of the prism body to an interior of the prism body, the first incident beam further is emitted to the junction surface. Then, the first incident beam is reflected from the junction surface to the light-emitting surface, is emitted out of the interior of the prism body through the light-emitting surface, and is emitted out of an interior of the housing through the first light-emitting port and the second light-emitting port. When a second incident beam is emitted through the third light penetrating surface of the prism body to the interior of the prism body, the second incident beam further is emitted to the first light penetrating surface. Then, the second incident beam is emitted out of the interior of the prism body from the first light penetrating surface, is emitted to the first accommodating space, is emitted through the urine in the first accommodating space, is emitted to the second light penetrating surface, is emitted to the interior of the prism body from the second light penetrating surface, is emitted to the third light penetrating surface, and is emitted out of the interior of the prism body from the third light penetrating surface. The glycosuria measurement device calculates a diopter according to the first incident beam out of the interior of the housing, calculates an absorbance according to the second incident beam out of the interior of the prism body, and calculates a glycosuria concentration according to the diopter and the absorbance.

As mentioned above, the glycosuria measurement device of the present invention simultaneously or independently detects the diopter and the absorbance of light and combines the light absorbance and the light refraction characteristic to analyze the glycosuria concentration in urine. Furthermore, the present invention can simplify an optical path alignment without a concentrator as a light source. Moreover, the glycosuria measurement device has a minimum volume without lens or eyepieces. In addition, the glycosuria measurement device reduces the manufacture cost without filters or polarizers. Besides, the glycosuria measurement device has multiple advantages for detecting glycosuria: without chemical agents, without test papers, without instruments to detect the urine so as to reduce the human errors, without oxidation and moisture caused by the degradation problems via the optical detection, improving the accuracy via the optical detection and test data collected easily to be analyzed and managed real time for health monitoring.

DETAILED DESCRIPTION OF THE INVENTION

Figure 1A:
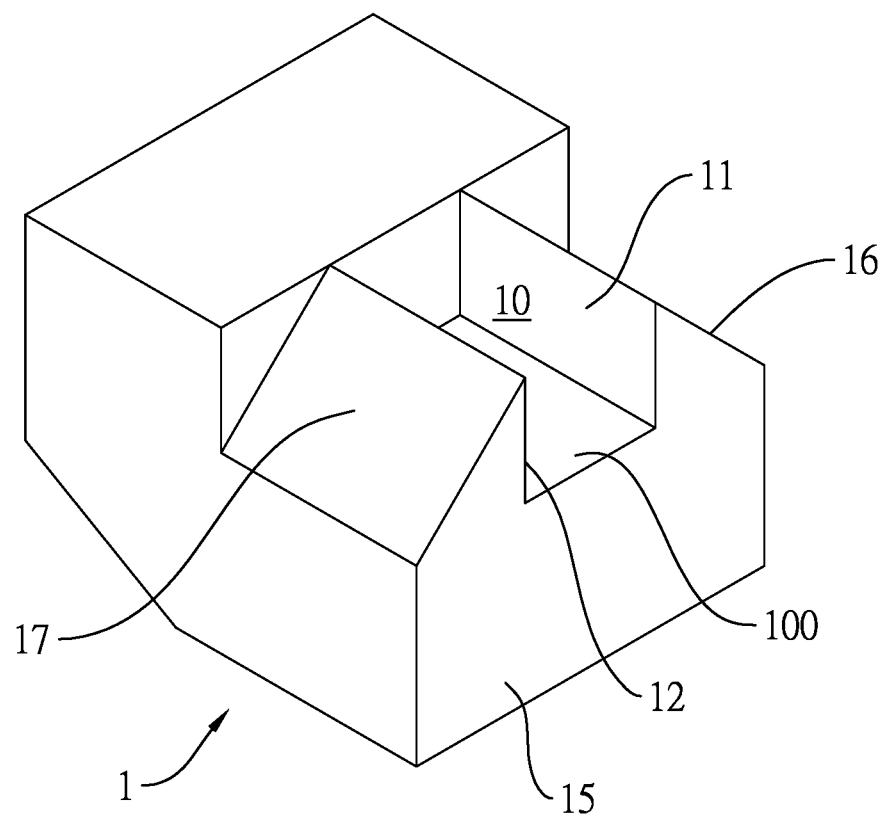
FIG. 1A and FIG. 1B are the first schematic diagram and the second schematic diagram of the prism body of the glycosuria measurement device of the present invention.
Figure 1B:
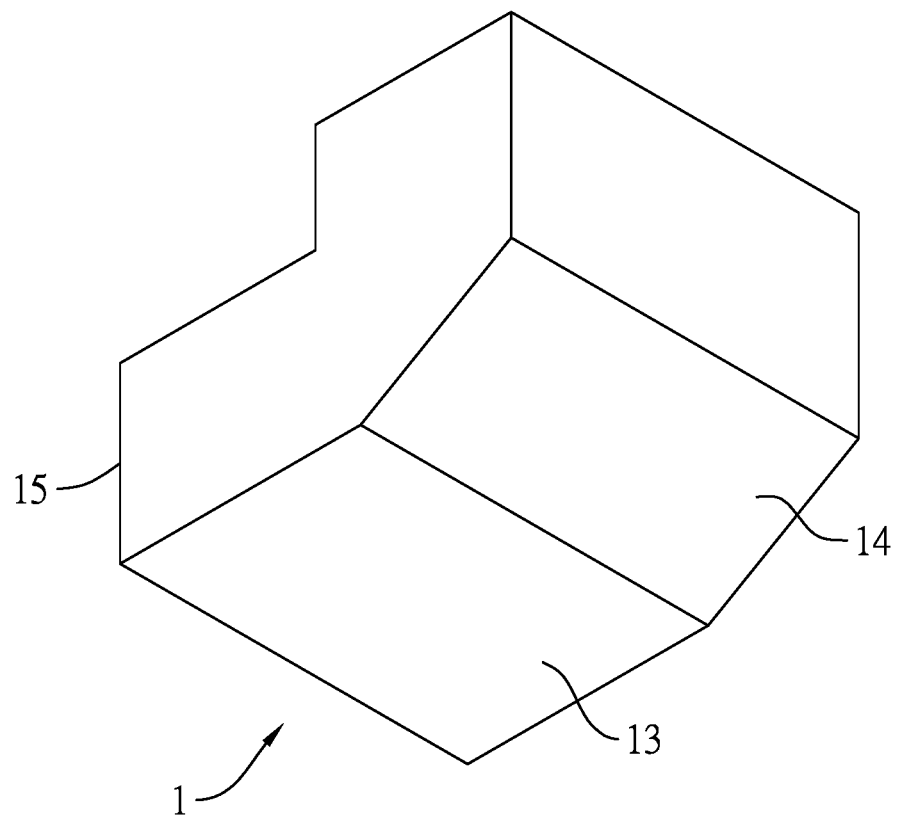

Refer to FIG. 1A and FIG. 1B. FIG. 1A and FIG. 1B are the first schematic diagram and the second schematic diagram of the prism body of the glycosuria measurement device of the present invention. The prism body 1 comprises a first accommodating space 10, a first light penetrating surface 11, a second light penetrating surface 12, a third light penetrating surface 13, and a light-emitting surface 14. The first accommodating space 10 accommodates urine Q. The junction surface 100 is formed at a bottom surface of the first accommodating space 10. The first light penetrating surface 11 is formed at a first lateral surface of the first accommodating space 10. The second light penetrating surface 12 is formed at a second lateral surface of the first accommodating space 10 opposite to the first light penetrating surface 11. The third light penetrating surface 13 is disposed opposite to the junction surface 100. The light-emitting surface 14 is disposed opposite to the junction surface 100.

Refer to FIG. 2A to FIG. 2D. FIG. 2A to FIG. 2D are the schematic diagram, the exploded view, the top view and the side view profile diagram of the glycosuria measurement device. The glycosuria measurement device 3 comprises the prism body 1 and a housing 2. The housing 2 comprises a second accommodating space 20, a first light-emitting port 21 and a second light-emitting port 22. The second accommodating space 20 accommodates the prism body 1. The first light-emitting port 21 has a first diameter, and is disposed relative to the light-emitting surface 14 of the prism body 1. The second light-emitting port 22 has a second diameter, and is disposed opposite to the first light-emitting port 21. The first diameter is less than or equal to the second diameter. In addition, in an embodiment of the present invention, the first light-emitting port 21 is a single slit. Further, a light-emitting space formed between the first light-emitting port 21 and the second light-emitting port 22 is trumpet-shaped. That is, the diameter from the first light-emitting port 21 to the second light-emitting port 22 is progressively larger. Besides, the housing 2 further comprises a start button 23, a display unit 24 and a power button 25. The start button 23 controls the first light source S1, the first light sensor D1, the second light source S2, the second light sensor D2 and the display unit 24 to be turned on or turned off. The display unit 24 displays the testing result of urine, that is, a value of glycosuria concentration. The power button 25 is electrically connected to a power supply unit (not shown in figures). The power supply unit is electrically connected to the start button 23, the display unit 24, the power button 25 and each light source to supply power to the elements.

Figure 2A:
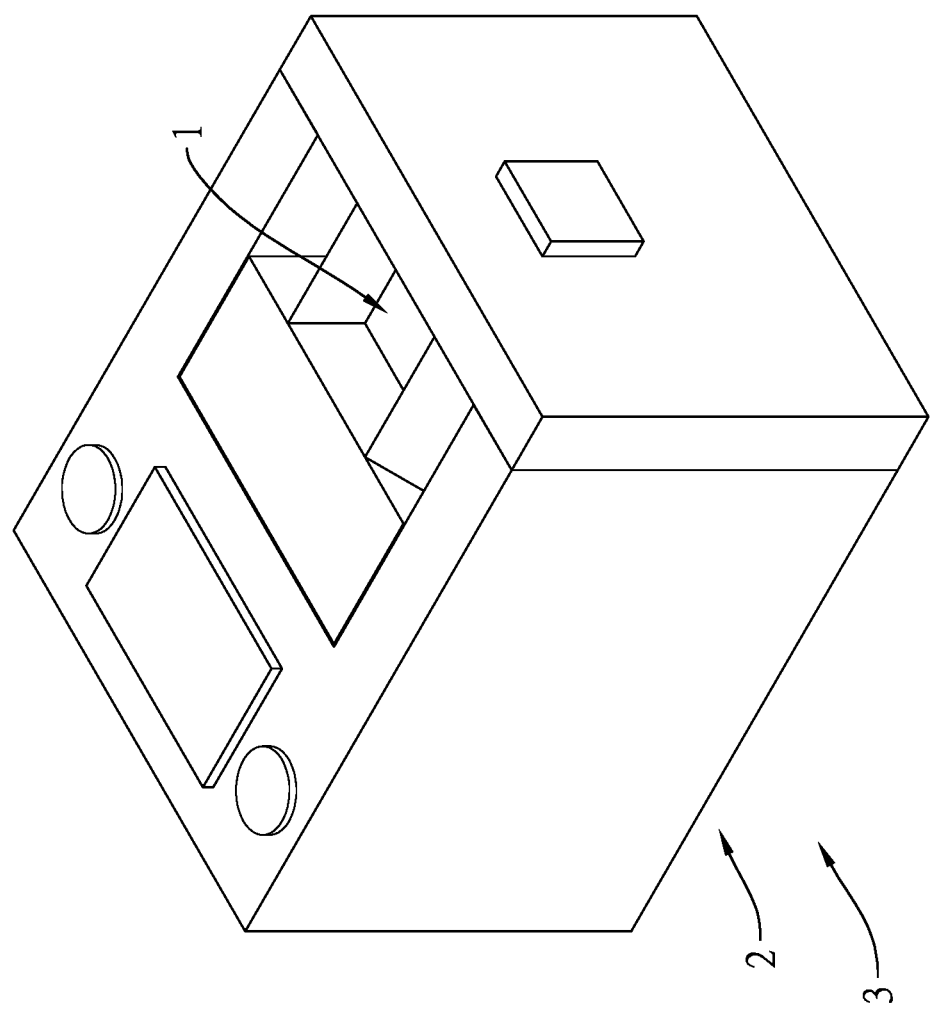
FIG. 2A to FIG. 2D are the schematic diagram, the exploded view, the top view and the side view profile diagram of the glycosuria measurement device.
Figure 2B:
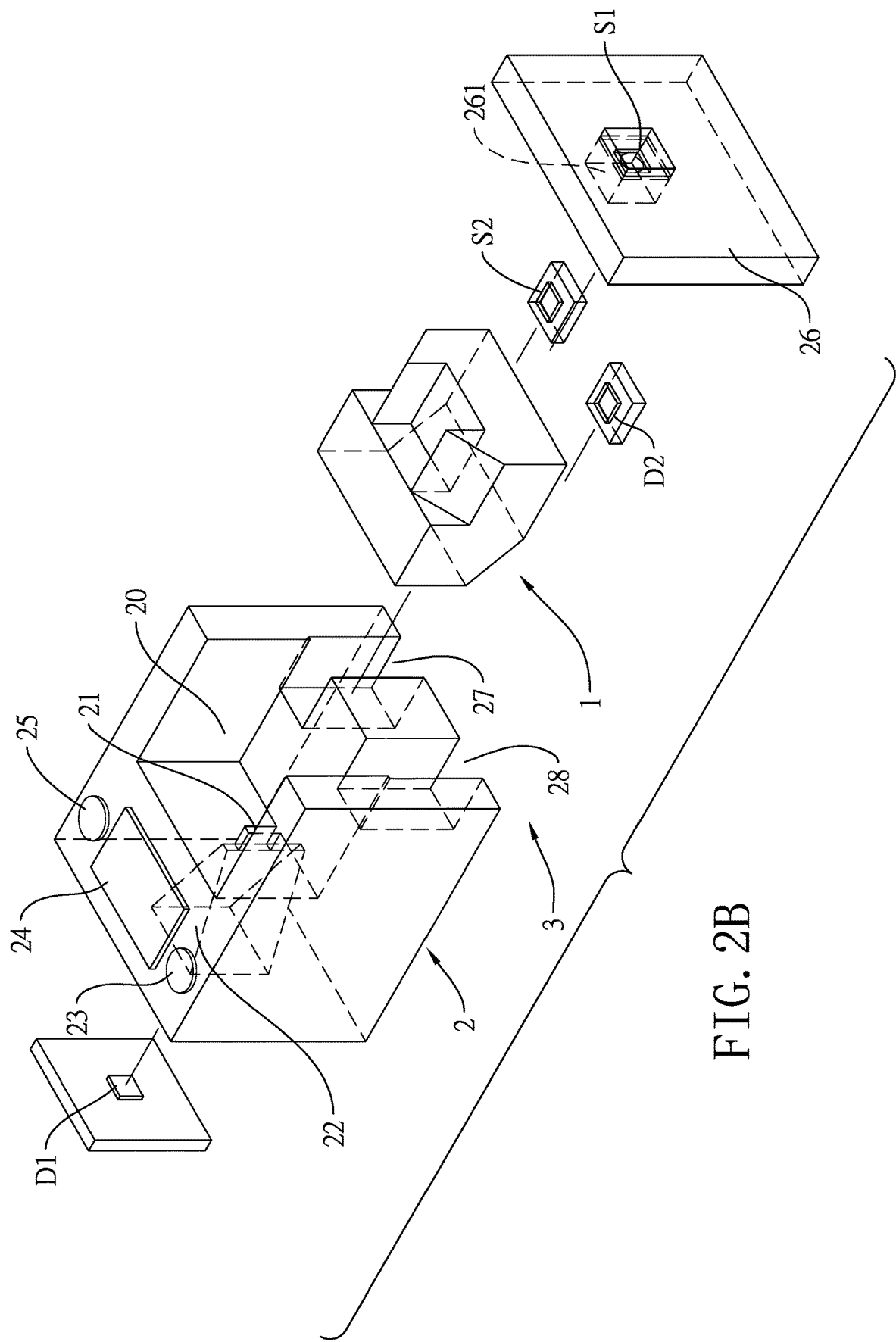
Figure 2C:
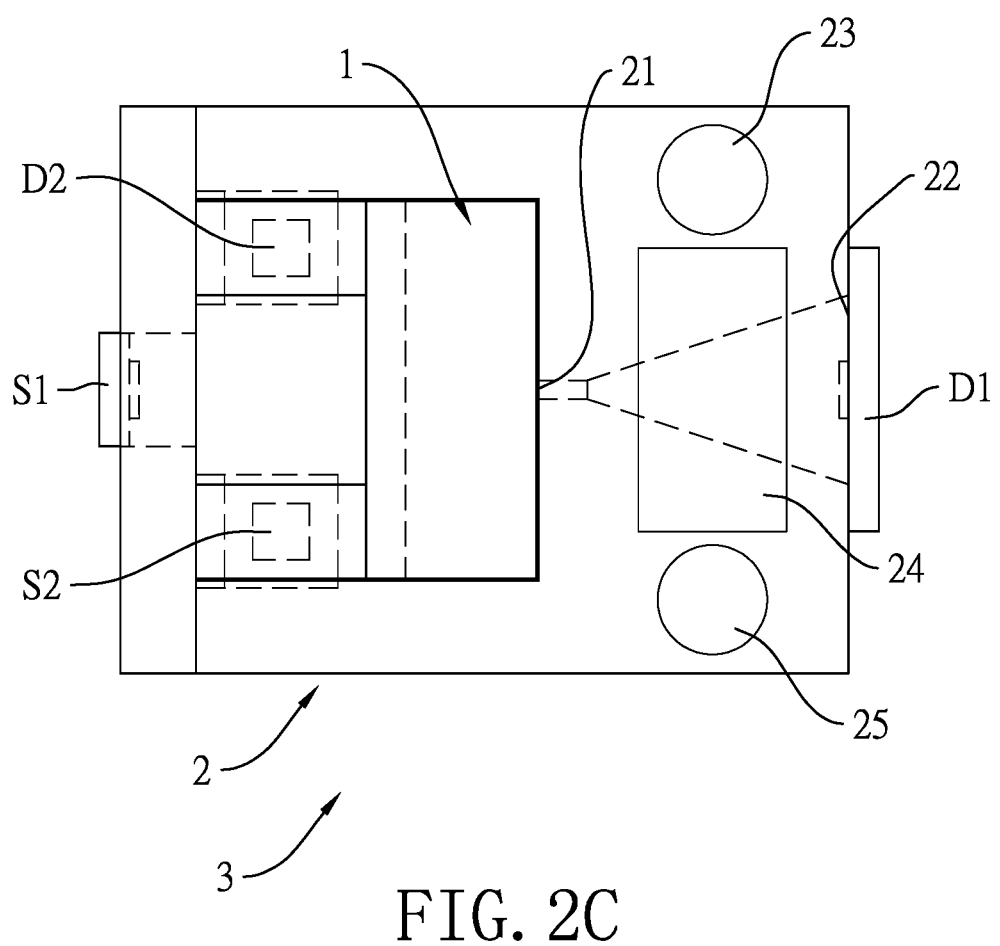

Refer to FIG. 2B. The glycosuria measurement device further comprises an exterior wall 26, a first light source S1, a first light sensor D1, a second light source S2 and a second light sensor D2. The exterior wall 26 is adhered to a surface of the housing 2 and the light-incident surface 15 (as shown in FIG. 1A) of the prism body 1 to form a first accommodating space 10 of the prism body 1. In detail, in an embodiment, since the first accommodating space 10 of the prism body 1 is an open space, the exterior wall 26 is adhered to the light-incident surface 15 of the prism body 1 so that the first accommodating space 10 is formed as an accommodating space accommodating urine. In another embodiment, the first accommodating space 10 of the prism body 1 is an enclosed space for accommodating urine. The first light source S1 is disposed on the exterior wall 26, below the junction surface 100, and generates the first incident beam L1. In other words, the first incident beam L1 is emitted to the junction surface 100 from bottom to top. The first light sensor D1 is disposed in the second light-emitting port 22 and receives the first incident beam L1, wherein a surface of the housing 2 is parallel to the second light-emitting port 22. The housing 2 further comprises a first accommodating slot 27 and a second accommodating slot 28. The second light source S2 is disposed in the first accommodating slot 27 of the housing 2 and generates the second incident beam L2. The second light sensor D2 is disposed in the second accommodating slot 28 of the housing 2 and receives the second incident beam L2. The first accommodating slot 27 is disposed parallel to the second accommodating slot 28.

Figure 2D:
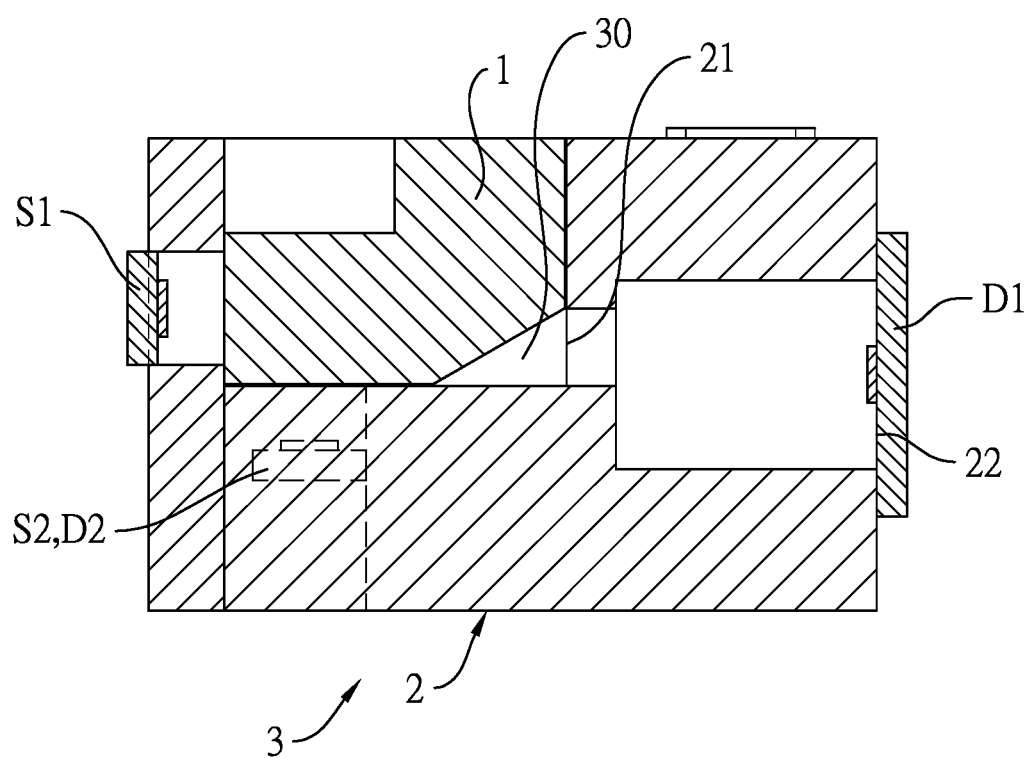

Refer to FIG. 2D. The empty space 30 is formed between the light-emitting surface 14 of the prism body 1 and the bottom surface of the second accommodating space 20 of the housing 2. The empty space 30 is a space for transmitting light. The first incident beam L1 is emitted out of the interior of the prism body 1 from the light-emitting surface 14 of the prism body 1, through the empty space 30, the first light-emitting port 21, the second light-emitting port 22, the interior of the housing 2, and is emitted to the first light sensor D1 disposed in the second light-emitting port 22.

Figure 3A:
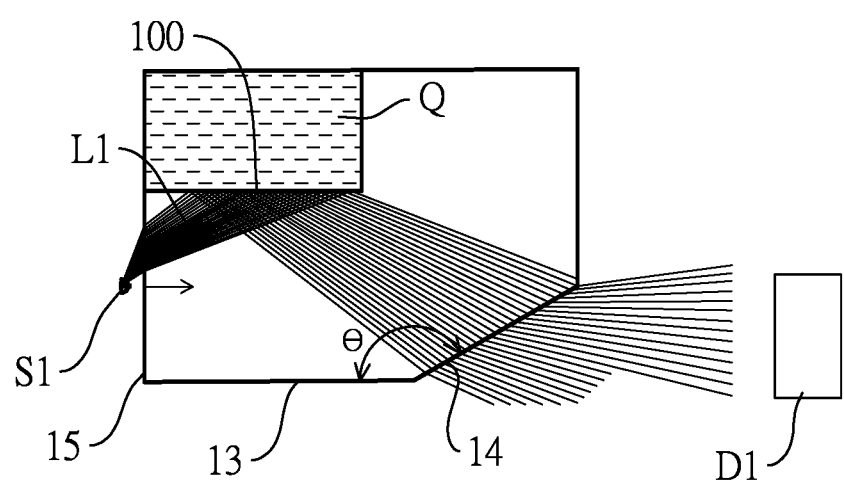
FIG. 3A and FIG. 3B are the light reflecting schematic diagram and light passing through urine schematic diagram of the glycosuria measurement device.
Figure 3B:
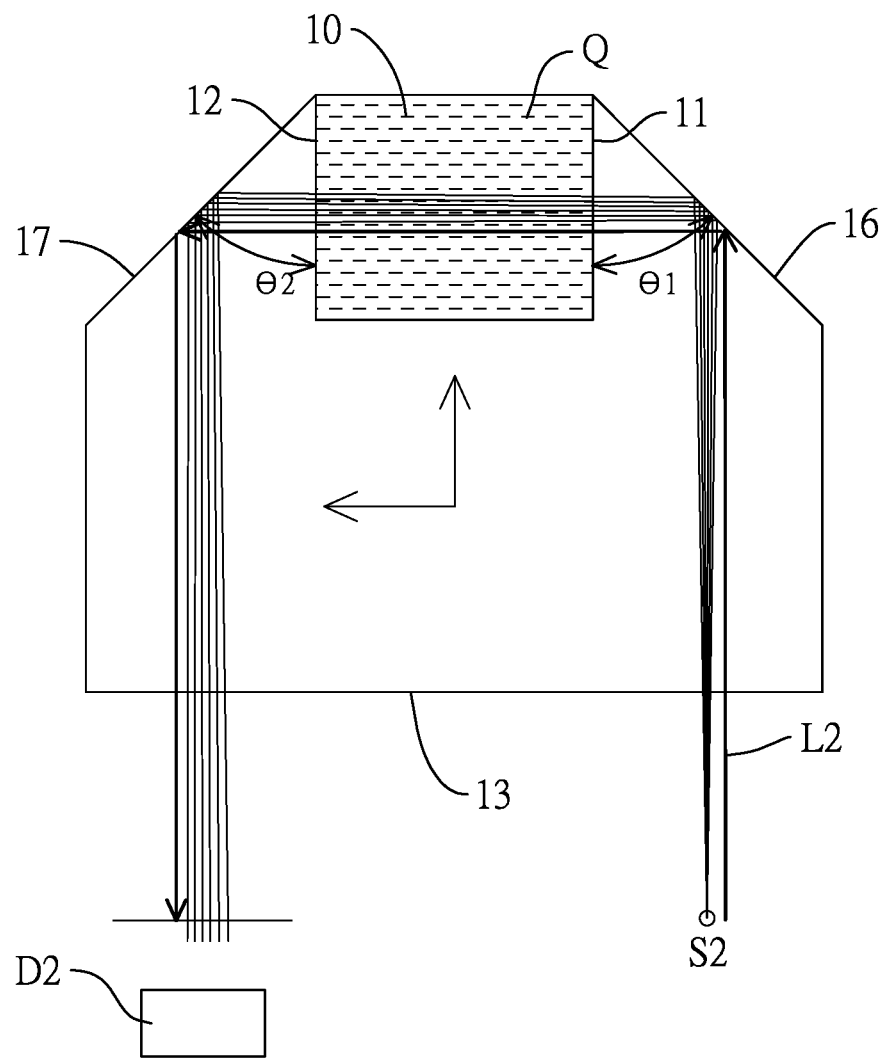

Refer to FIG. 3A and FIG. 3B. FIG. 3A and FIG. 3B are the light reflecting schematic diagram and light passing through urine schematic diagram of the glycosuria measurement device. As shown in FIG. 3A with reference to FIG. 2D, the first light source S1 generates the first incident beam L1 emitted to the interior of the prism body 1. The first incident beam L1 is emitted to the junction surface 100 and reflected from the junction surface 100 to the light-emitting surface 14. The first incident beam L1 is emitted out of the light-emitting surface 14 from the interior of the prism body 1 and through the first light-emitting port 21 and the second light-emitting port 22 to the first light sensor D1 disposed in the light-emitting port 22 of the housing 2 to measure the diopter of urine Q. As shown in FIG. 3B with reference to FIG. 2B, the second light source S2 generates the second incident beam L2 emitted to the interior of the prism body. The second incident beam L2 is emitted to the first light penetrating surface 11 and out of the interior of the prism body from the first light penetrating surface 11. The second incident beam L2 is emitted to the first accommodating space 10, emitted through urine Q in the first accommodating space 10, emitted to the second light penetrating surface 12, emitted to the interior of the prism body from the second light penetrating surface 12, emitted to the third light penetrating surface 13, emitted out of the interior of the prism body from the third light penetrating surface 13, and emitted to the second light sensor D2 disposed in the housing 2. The concentration of urine Q is calculated for measuring the first incident beam L1 through the light-emitting surface 14, the first light-emitting port 21 and the second light-emitting port 22 by the first light sensor D1. The absorbance of urine Q is calculated for measuring the second incident beam D2 through the third light penetrating surface 13 by the second light sensor D2.

As mentioned above, according to the optical principle, when light is emitted to different materials, light will be refracted and reflected. Hence, the first light sensor D1 is disposed in the second light-emitting port 22 of the housing to calculate the concentration of urine Q by measuring the reflected first incident beam L1 (diopter). In addition, when light passes through urine Q, urine Q will absorb the light energy so as to reduce the light intensity. Therefore, the second light sensor D2 is disposed in the housing to calculate the absorbance of urine Q by measuring the received second incident beam L2.

As shown in FIG. 1A, FIG. 1B and FIG. 3A, the prism body 1 further comprises a light-incident surface 15, adjacent to the junction surface 100. In an embodiment of the present invention, the light-incident surface 15 is perpendicularly adjacent to the junction surface 100. The first incident beam L1 generated by the first light source S1 is emitted to the interior of the prism body 1 through the light-incident surface 15 and is emitted to the junction surface 100.

As shown in FIG. 1A, FIG. 1B and FIG. 3B, the third light penetrating surface 13 is adjacent to the light-incident surface 15. In an embodiment of the present invention, the third light penetrating surface 13 is perpendicularly adjacent to the light-incident surface 15. The second incident beam L2 is emitted to the interior of the prism body 1 from the third light penetrating surface 13 and is emitted to the first light penetrating surface 11.

As shown in FIG. 3A, the light-emitting surface 14 is adjacent to the third light penetrating surface 13. The light-emitting surface 14 and the light-incident surface 15 are adjacent to two opposite sides of the third light penetrating surface 13. An intersection angle θ is formed between the light-emitting surface 14 and the third light penetrating surface 13. The intersection angle θ is an obtuse angle, between 105 degrees and 165 degrees. In a best mode of the present invention, the intersection angle θ is 135 degrees.

Referring to FIG. 3B, the prism body 1 further comprises a first light-reflecting surface 16 and a second light-reflecting surface 17. When the second incident beam L2 generated by the second light source S2 is emitted to the interior of the prism body 1, the second incident beam L2 is emitted to the first light-reflecting surface 16. Then, the second light source S2 is reflected by the first light-reflecting surface 16, is emitted to the first light penetrating surface 11, is emitted out of the interior of the prism body 1 from the first light penetrating surface 11, is emitted to the first accommodating space 10, is emitted through urine Q in the first accommodating space 10, is emitted to the second light penetrating surface 12, is emitted to the interior of the prism body 1 from the second light penetrating surface 12, is emitted to the second light-reflecting surface 17, is reflected by the second light-reflecting surface 17 reflect, is emitted to the third light penetrating surface 13, is emitted out of the interior of the prism body 1 from the third light penetrating surface 13, and is emitted to the second light sensor D2 disposed in the housing 2. The first light-reflecting surface 16 is adjacent to the first light penetrating surface 11. A first intersection angle θ1 is between the first light penetrating surface 11 and the first light-reflecting surface 16, wherein the first intersection angle θ1 is an acute angle, between 15 degrees and 75 degrees. In a best mode of the present invention, the first intersection angle θ1 is 45 degrees. The first light-reflecting surface 16 is disposed at the first intersection angle θ1 according to the angle at which the second incident beam L2 is emitted to the third light penetrating surface 13. The second light-reflecting surface 17 is adjacent to the second light penetrating surface 12. A second intersection angle θ2 is between the second light penetrating surface 12 and the second light-reflecting surface 17. The second intersection angle θ2 is an acute angle, between 15 degrees and 75 degrees. In a best mode of the present invention, the second intersection angle θ2 is 45 degrees. The second light-reflecting surface 17 is disposed at the second intersection angle θ2 according to the angle at which the second incident beam L2 is reflected from the first light-reflecting surface 16.

Refer to FIG. 3A and FIG. 3B again. In an embodiment of the present invention, the first light-reflecting surface 16 and the second light-reflecting surface 17 of the prism body 1 are triangular in shape, are respectively disposed around two lateral surfaces of the first accommodating space 10, and form the first accommodating space 10 with the junction surface 100 (bottom surface) of the first accommodating space 10. It should be noted that, in the figures, the first accommodating space 10 cannot form an enclosed space with a first triangular block, a second triangular block and another triangular block. When the prism body 1 is disposed in the second accommodating space 20 of the housing 2, the light-incident surface 15 of the prism body 1 is adhered to the wall of the second accommodating space 20 of the housing 2 to enclose the first accommodating space 10 of the prism body 1 as an enclosed space to accommodate urine Q.

Figure 4A:
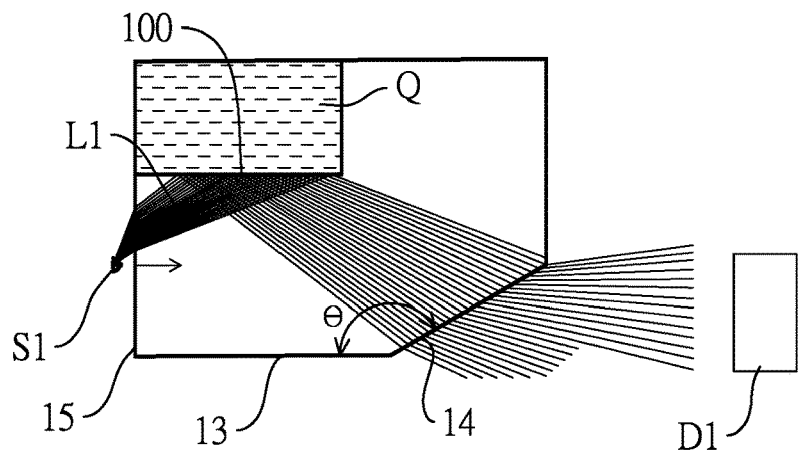
FIG. 4A to FIG. 4C are the reflected light schematic diagrams of the glycosuria measurement device of the present invention.
Figure 4B:
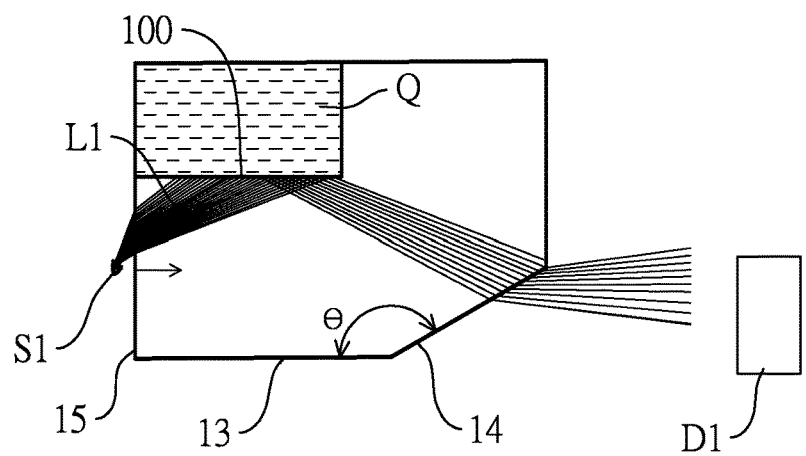
Figure 4C:
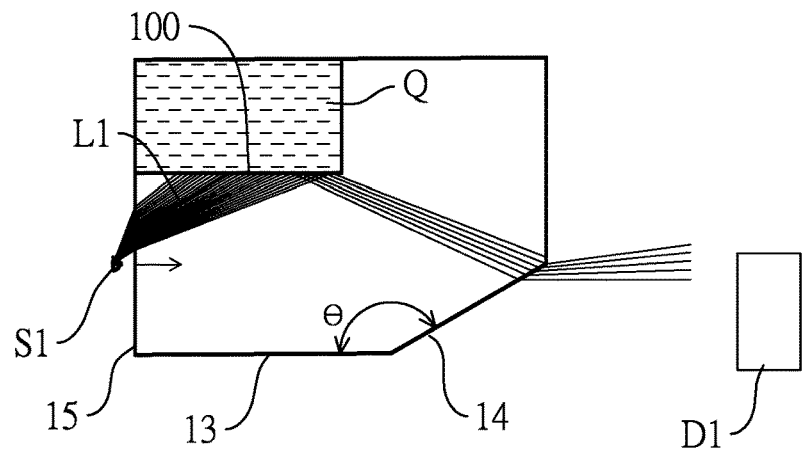

Refer to FIG. 4A to FIG. 4C. FIG. 4A to FIG. 4C are the reflected light schematic diagrams of the glycosuria measurement device of the present invention. As shown in figures, the light-emitting surface 14 of the prism body 1 is disposed at the other side opposite to the light-incident surface 15. The first incident beam L1 reflected by the junction surface 100 passes through the light-emitting surface 14, the first light-emitting port 21 and the second light-emitting port 22 of the housing 2, and is emitted to the first light sensor D1. It is well known that the angle and the area of the light-emitting surface 14 and the diameter of the first light-emitting port 21 and the second light-emitting port 22 need to be arranged to measure the first incident beam L1 passing through the light-emitting surface 14, the first light-emitting port 21 and the second light-emitting port 22. In detail, according to Snell's Law, as the medium refractive index of the prism body 1 and the incidence angle of the first incident beam L1 emitted to the junction surface 100 are known, the medium refractive index of urine Q can be calculated according to the reflected angle formed by the first incident beam L1 passing through the junction surface 100 of different medium refractive indexes (different solutions). If the refractive index of urine Q increases, the refracted light will increase. In contrast, if the reflected light decreases, the reflected first incident beam L1 received by the first light sensor D1 will decrease (as shown in FIG. 4A and FIG. 4B). As a result, the predetermined inclined angle θ and the predetermined area of the light-emitting surface 14 and the diameter of the first light-emitting port 21 and the second light-emitting port 22 can be arranged and disposed according to the reflected first incident beam L1 (diopter) emitted to the medium refractive index of different urines Q. That is, the predetermined inclined angle θ of the light-emitting surface 14 is disposed based on the position of the junction surface 100.

In a best mode of the present invention, the first light source S1 is disposed in a puncture 261 of the exterior wall 26 of the housing 2 and corresponds to a normal line perpendicular to the center of the light-incident surface 15 of the prism body 1 so that the first incident beam L1 can be uniformly emitted to the light-incident surface 15. The first light sensor D1 is disposed in the second light-emitting port 22 of the housing 2 so as to uniformly receive the first incident beam L1 passing through the light-emitting surface 14, the first light-emitting port 21 and the second light-emitting port 22.

Figure 5A:
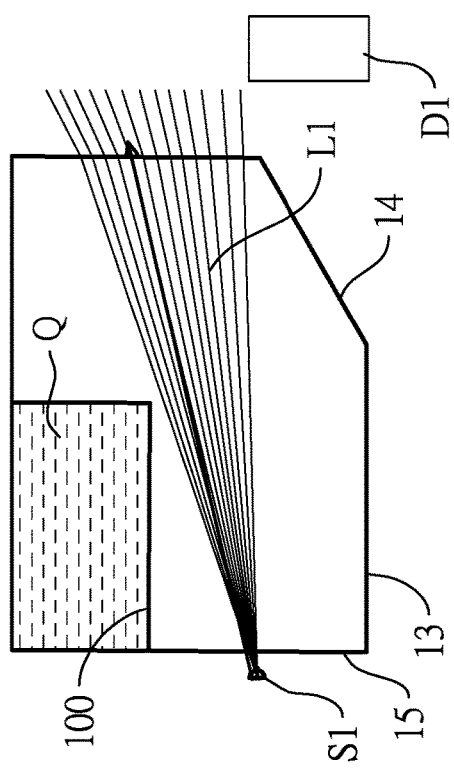
FIG. 5A to FIG. 5D are the schematic diagrams of the first incident beam emitted to the glycosuria measurement device.
Figure 5B:
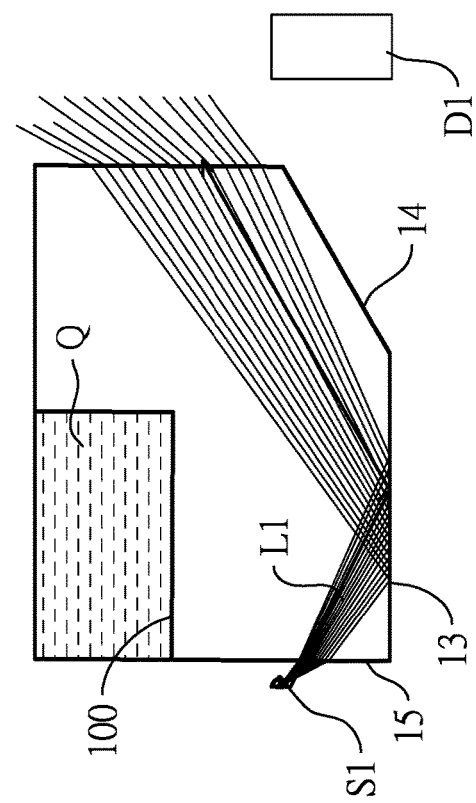
Figure 5C:
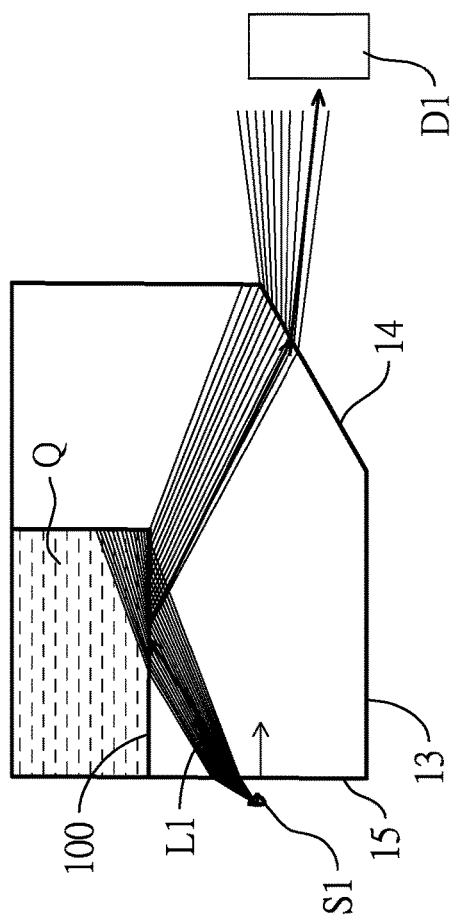
Figure 5D:
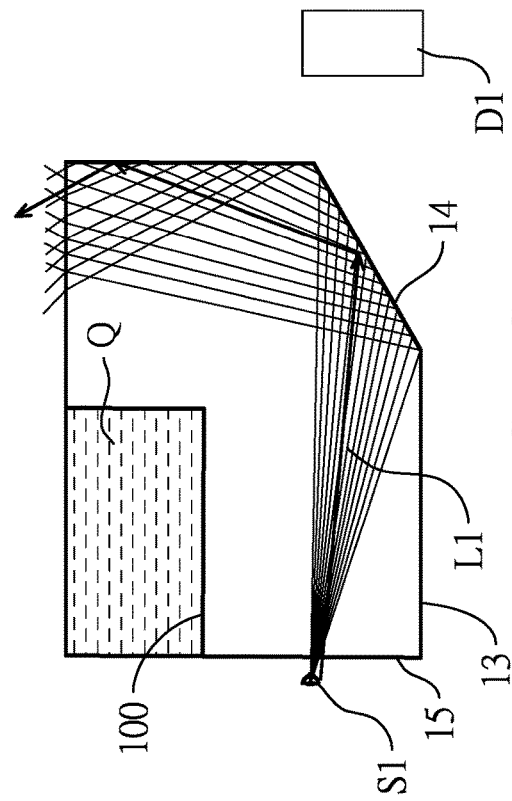

Refer to FIG. 5A to FIG. 5D. FIG. 5A to FIG. 5D are the schematic diagrams of the first incident beam emitted to the glycosuria measurement device. In fact, in an embodiment of the present invention, for measuring the reflected first incident beam L1 emitted to the prism body 1 and measuring the second incident beam L2 passing through urine Q, the first light source S1 and the second light source S2 comprise a halogen Lamp, a gas lamp, a laser lamp, an LED, or other light emission elements. For the first incident beam L1 emitted to the prism body 1 and reflected from the prism body 1, since the beam generated by the light source is emitted outwards for 360 degrees, for a half of the light emitted to the prism body 1, the beam can be distinguished into four parts of light as shown in FIG. 5A to FIG. 5D. As shown in FIG. 5A, when the first incident beam L1 is emitted to the junction surface 100 of the prism body 1, the reflected first incident beam L1 is emitted out of the light-emitting surface 14 and is emitted to the first light sensor D1. As shown in FIG. 5B, when the first incident beam L1 is emitted to the prism body 1, since the prism body 1 has no other surfaces or other junction surfaces 100 to reflect the first incident beam L1, the incident beam is emitted out of the prism body 1. As shown in FIG. 5C, when the first incident beam L1 is emitted to the light-emitting surface 14 of the prism body 1, the incident angle of the first incident beam L1 exactly matches the angle of the light-emitting surface 14 to form the angle of a total reflection so that the reflect first incident beam L1 is emitted to other surfaces of the prism body 1 and is emitted out of the prism body 1. As shown in FIG. 5D, when the first incident beam L1 is emitted to the third light penetrating surface 13 of the prism body 1, the reflected first incident beam L1 is emitted to a surface other than the light-emitting surface 14. Accordingly, the first light sensor D1 disposed in the second light-emitting port 22 receives the reflected first incident beam L1 emitted to the junction surface 100 of the prism body 1.

Figure 6:
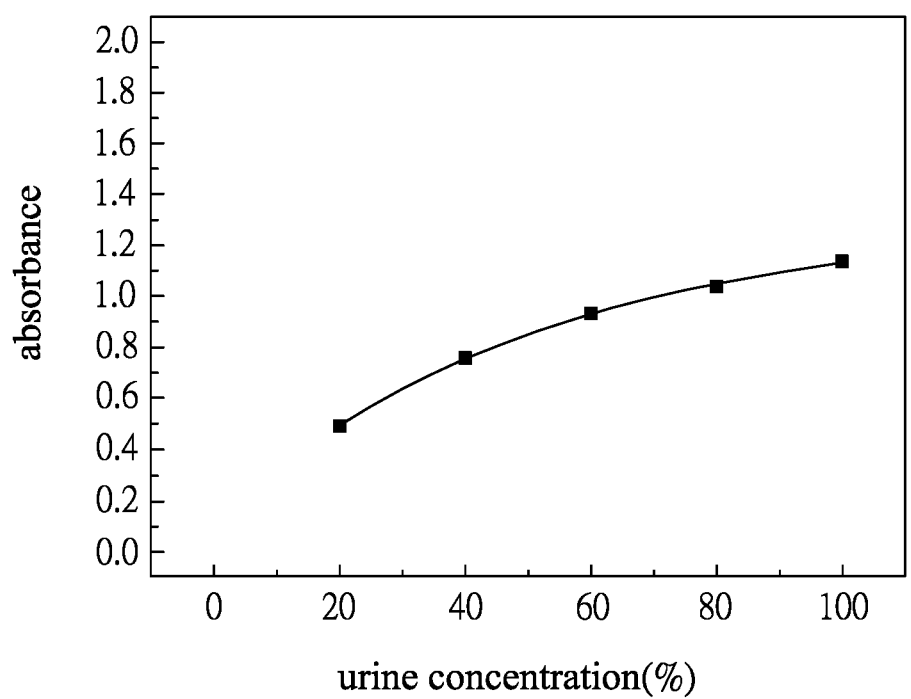
FIG. 6 is the schematic diagram regarding the urine concentration and the absorbance.

Refer to FIG. 6. FIG. 6 is the schematic diagram regarding the urine concentration and the absorbance. Since the absorbance varies with the urine Q concentration, the urine Q concentration can be calculated by measuring the absorbance of urine Q. According to Beer Lambert law, when a parallel light is perpendicularly emitted to a sample, the absorbance material of the sample absorbs a part of photon energy so as to reduce the intensity of the light. The absorbed energy (A), the absorbance coefficient of the sample (α), optical path (length of sample) (L), and the concentration (c) have a positive relationship. The relationship is represented by the formula below:

$$A = \alpha L c$$

The absorbed energy is regarded as an absorbance (A). When light passes through the sample and one part of light energy is absorbed by the sample, the other part of light passes through the sample. Therefore, the absorbance of the sample can be calculated by the value of the energy difference between the incident light (I0) and the transmission light (I). The absorbance is defined by the formula below:

$$A = -\log \frac{I}{I_0}$$

Besides, the second incident beam L2 is emitted to the first light-reflecting surface 16, reflected by the first light-reflecting surface 16, and passing through urine Q. A part of the photon energy of the second incident beam L2 is absorbed by urine Q so that the intensity of the transmission light is weak. After that, the transmission light is reflected by the second light-reflecting surface 17 and is emitted to the second light sensor D2. If the concentration of urine Q increases, the energy absorbed by urine Q increases, and the intensity of the transmission light decreases. The absorbance can be determined between the intensity of the light source and the proportion of the transmission light to calculate the concentration of urine Q.

Figure 7:
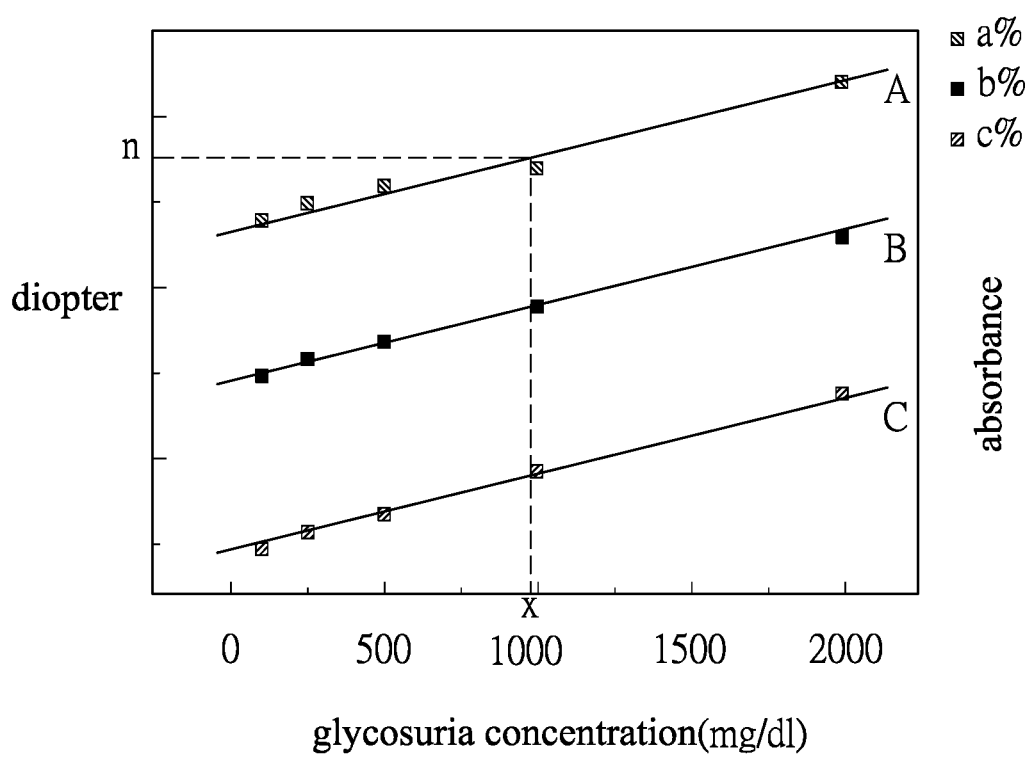
FIG. 7 is the schematic diagram regarding the absorbance and the diopter of the glycosuria concentration of the present invention.

Refer to FIG. 7. FIG. 7 is the schematic diagram regarding the absorbance and the diopter of the glycosuria concentration of the present invention. If the concentration of urine Q varies, the light absorbance changes. Consequently, different urine concentration curves have different glycosuria characteristic curves A, B, C. The invention determines the glycosuria characteristic curves A, B, C via measuring the absorbance of urine. The invention further determines the refractive index via measuring light passing through urine Q: the diopter of urine. Accordingly, the invention calculates the glycosuria concentration according to the refractive index and the absorbance of urine corresponding to the glycosuria characteristic curves A, B, C. In an embodiment of the present invention, the housing 2 further comprises a storage module (not shown in the figure), storing a database. The database comprises multiple glycosuria characteristic curves, which are facilitated for the processor to calculate and compare the glycosuria concentrations.

For instance, the glycosuria characteristic curve A corresponds to the absorbance a, the glycosuria characteristic curve B corresponds to the absorbance b, and the glycosuria characteristic curve C corresponds to the absorbance c, wherein a>b>c. The value of the urine diopter measured by the glycosuria measurement device of the present invention is n. Accordingly, the present invention calculates the corresponding glycosuria concentration as x (mg/dl) according to the aforementioned embodiments. That is, the glycosuria characteristic curve A is determined by the absorbance a calculated by the formula and calculates the diopter as n according to the glycosuria characteristic curve A.

Figure 8:
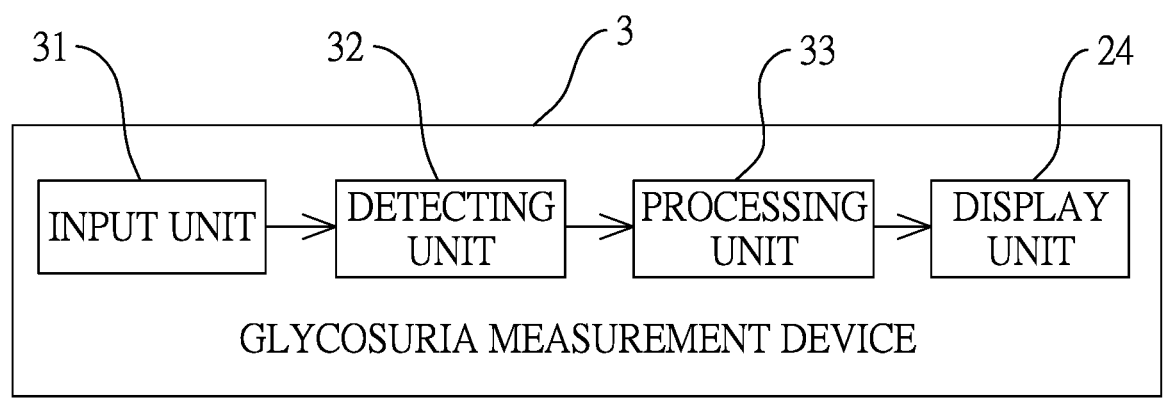
FIG. 8 is the block schematic diagram of the glycosuria measurement device of the present invention.

Refer to FIG. 8. FIG. 8 is the block schematic diagram of the glycosuria measurement device of the present invention. The glycosuria measurement device 3 further comprises an input unit 31, a detecting unit 32 and a processing unit 33. The input unit 31 is electrically connected to a power supply unit, comprising the first light source S1 and the second light source S2. The input unit 31 generates an initiate signal to trigger the first light source S1 and the second light source S2. The detecting unit 32 comprises the first light sensor D1 and the second light sensor D2, which are electrically connected to the power supply unit and the input unit 31, and respectively receive and sense the first incident beam L1 and the second incident beam L2 generated by the first light source S1 and the second light source S2. The first incident beam L1 and the second incident beam L2 pass through urine and the junction surface 100 of the prism body 1 to generate a transmission light, a reflected light and a refracted light. The processing unit 33 is electrically connected to the detecting unit 32 and the display unit 24, calculates the diopter according to the first incident beam L1 received by the first light sensor D1, and calculates the absorbance according to the second incident beam L2 received by the second light sensor D2. The processing unit 33 further calculates glycosuria concentration according to the diopter and the absorbance. Then, the glycosuria concentration is displayed on the display unit 24.

In an embodiment of the present invention, the materials of the prism body 1 comprise glass, plastic, or other translucent materials. The junction surface 100, the first light penetrating surface 11, the second light penetrating surface 12, the third light penetrating surface 13, the light-emitting surface 14, the light-incident surface 15, the first light-reflecting surface 16, and the second light-reflecting surface 17 of the prism body 1 are smooth surfaces, rough surfaces, coated surfaces, blocking surfaces, or other machining surfaces. The prism body 1 can be manufactured by grinding, adhesive bonding, molding, injection moulding, or other processing methods.

In an embodiment of the present invention, each of the first light sensor D1 and the second light sensor D2 comprises a photodetection diode, a photodetection diode array, a spectrometer, a charge-coupled device (CCD) sensor, or other charge-coupled devices.

In summary, the glycosuria measurement device of the present invention simultaneously or independently detects the diopter and the absorbance of light and combines the light absorbance and the light refraction characteristic to analyze the glycosuria concentration of urine. Furthermore, the present invention can simplify an optical path alignment without a concentrator as a light source. Moreover, the glycosuria measurement device has a minimum volume without lens or eyepieces. In addition, the glycosuria measurement device reduces the manufacture cost without filters or polarizers. Besides, the glycosuria measurement device has multiple advantages for detecting glycosuria: without chemical agents, without test papers, without instruments to detect the urine so as to reduce the human errors, without oxidation and moisture caused by the degradation problems via the optical detection, improving the accuracy via the optical detection and test data collected easily to be analyzed and managed real time for health monitoring.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:
1. A glycosuria measurement device, comprising:
 a prism body, comprising:
  a first accommodating space, configured to accommodate urine;
  a junction surface, formed at a bottom surface of the first accommodating space;
  a first light penetrating surface, formed at a first lateral surface of the first accommodating space;
  a second light penetrating surface, formed at a second lateral surface of the first accommodating space; wherein the second light penetrating surface is opposite to the first light penetrating surface;
  a third light penetrating surface, disposed opposite to the junction surface;
  a light-emitting surface, disposed opposite to the junction surface;
  a light-incident surface, disposed adjacent to the junction surface; and
 a housing, comprising:
  a second accommodating space, configured to accommodate the prism body;
  a first light-emitting port, having a first diameter and disposed opposite to the light-emitting surface of the prism body;
  a second light-emitting port, having a second diameter and disposed opposite to the first light-emitting port;
  wherein the first diameter is less than or equal to the second diameter;
 wherein when a first incident beam is emitted through the light-incident surface of the prism body to an interior of the prism body, the first incident beam further is emitted to the junction surface, reflected from the junction surface to the light-emitting surface, emitted out of the interior of the prism body through the light-emitting surface, and emitted out of an interior of the housing through the first light-emitting port and the second light-emitting port;
 wherein when a second incident beam is emitted through the third light penetrating surface of the prism body to the interior of the prism body, the second incident beam further is emitted to the first light penetrating surface, emitted out of the interior of the prism body from the first light penetrating surface, emitted to the first accommodating space, emitted through the urine in the first accommodating space, emitted to the second light penetrating surface, emitted to the interior of the prism body from the second light penetrating surface, emitted to the third light penetrating surface, and emitted out of the interior of the prism body from the third light penetrating surface;
 wherein the glycosuria measurement device calculates a diopter according to the first incident beam out of the interior of the housing, calculates an absorbance according to the second incident beam out of the interior of the prism body, and calculates a glycosuria concentration according to the diopter and the absorbance.

2. The glycosuria measurement device of claim 1, wherein the third light penetrating surface is adjacent to the light-incident surface.

3. The glycosuria measurement device of claim 2, wherein the light-emitting surface is adjacent to the third light penetrating surface, and the light-emitting surface and the light-incident surface are adjacent to opposite sides of the third light penetrating surface.

4. The glycosuria measurement device of claim 3, further comprising:
 a first light-reflecting surface, being adjacent to the first light penetrating surface;
 a second light-reflecting surface, being adjacent to the second light penetrating surface;
 wherein when the second incident beam is emitted to the interior of the prism body, the second incident beam is emitted to the first light-reflecting surface, reflected by the first light-reflecting surface, emitted to the first light penetrating surface, emitted out of the interior of the prism body from the first light penetrating surface, emitted to the first accommodating space, emitted through the urine in the first accommodating space, emitted to the second light penetrating surface, emitted to the interior of the prism body from the second light penetrating surface, emitted to the second light-reflecting surface, reflected by the second light-reflecting surface, emitted to the third light penetrating surface, and emitted out of the interior of the prism body from the third light penetrating surface.

5. The glycosuria measurement device of claim 1, wherein a light-emitting space formed between the first light-emitting port and the second light-emitting port is trumpet-shaped.

6. The glycosuria measurement device of claim 1, wherein the first light-emitting port is a single slit.

7. The glycosuria measurement device of claim 1, further comprising:
   an exterior wall, adhering to a surface of the housing and the light-incident surface of the prism body and having a puncture;
   a first light source, disposed in the puncture on the exterior wall opposite to the light-incident surface of the prism body and generating the first incident beam;
   a first light sensor, disposed in the second light-emitting port and receiving the first incident beam;
   a second light source, disposed in a first accommodating slot of the housing and generating the second incident beam; and
   a second light sensor, disposed in a second accommodating slot of the housing and receiving the second incident beam;
   wherein the first accommodating slot is parallel to the second accommodating slot.

8. The glycosuria measurement device of claim 1, wherein the light-emitting surface and a bottom surface of the second accommodating space form an empty space so that the first incident beam is emitted out of the interior of the prism body from the light-emitting surface, is emitted out of the interior of the housing through the empty space, the first light-emitting port, and the second light-emitting port.

9. The glycosuria measurement device of claim 8, wherein the housing comprises:
   a start button, initiating at least one light source;
   a display unit, displaying a measurement result of the urine; and
   a power button, electrically connected to a power supply unit and the power supply unit electrically connected to the display unit and the start button.

10. The glycosuria measurement device of claim 9, further comprising a processing unit, electrically connected to the power supply unit, the first light sensor and the second light sensor, calculating the diopter according to the first incident beam received by the first light sensor, calculating the absorbance according to the second incident beam received by the second light sensor, and calculating the glycosuria concentration according to the diopter and the absorbance.

\* \* \* \* \*